United States Patent [19]
Rich

[11] Patent Number: 6,123,674
[45] Date of Patent: Sep. 26, 2000

[54] AIRWAY VALVE TO FACILITATE RE-BREATHING, METHOD OF OPERATION, AND VENTILATOR CIRCUIT SO EQUIPPED

[75] Inventor: David R. Rich, Glastonbury, Conn.

[73] Assignee: NTC Technology Inc., Wilmington, Del.

[21] Appl. No.: 09/173,518

[22] Filed: Oct. 15, 1998

[51] Int. Cl.⁷ .............................. A61B 5/08; A62B 9/02; A61M 16/00
[52] U.S. Cl. ...................... 600/529; 600/532; 600/538; 128/205.24; 128/207.16
[58] Field of Search .................. 600/529, 531, 600/532, 533, 537, 538, 543; 128/200.24, 200.27, 201.28, 205.13, 205.23, 205.24, 207.12, 207.16, 914; 137/512.11

[56] References Cited

U.S. PATENT DOCUMENTS

| | | |
|---|---|---|
| 3,556,122 | 1/1971 | Laerdal . |
| 3,568,977 | 3/1971 | Nelson . |
| 3,643,686 | 2/1972 | Koegel . |
| 3,795,257 | 3/1974 | Fabish et al. . |
| 3,812,878 | 5/1974 | Bird et al. . |
| 3,859,997 | 1/1975 | Douma et al. . |
| 3,902,516 | 9/1975 | Rudolph . |
| 3,910,261 | 10/1975 | Ragsdale et al. . |
| 3,933,171 | 1/1976 | Hay . |
| 3,942,547 | 3/1976 | Pfitzner . |
| 3,993,059 | 11/1976 | Siostrand . |
| 4,111,228 | 9/1978 | Simionescu . |
| 4,190,045 | 2/1980 | Bartels . |
| 4,192,301 | 3/1980 | Hardwick . |

(List continued on next page.)

FOREIGN PATENT DOCUMENTS

WO 98/12963   4/1998   WIPO .

OTHER PUBLICATIONS

John M. Capek et al., "Noninvasive Measurement of Cardiac Output Using Partial $CO_2$ Rebreathing", IEEE Transactions on Biomedical Engineering, vol. 35, No. 9, Sep1988, pp. 653–661.

John M. Cepak, "Noninvasive Measurement of Cardiac Output Using Partial Carbon–Dioxide Rebreathing", UMI Dissertation Services, Dec. 1988, pp. 126–132.

Marvin A. Sackner, "Measurement of Cardiac Output by Alveolar Gas Exchange", Chapter 13: Pulmonary Capillary Blood Flow of the Handbook of Physiology—The Respiratory System IV, pp. 233–255.

(List continued on next page.)

*Primary Examiner*—Cary O'Connor
*Assistant Examiner*—Navin Natnithithadha
*Attorney, Agent, or Firm*—Trask, Britt & Rossa

[57] ABSTRACT

An airway valve, method of operation and ventilator circuit including the valve. The airway valve includes an outer housing defining a primary passage including first and second coaxial primary passage portions mutually directly communicating within the housing, and first and second diversion passages extending transversely to the primary passage, each diversion passage being integral with the housing and opening onto a primary passage portion. The airway valve controls diversion of air flow between the first primary passage portion and the second primary passage portion into and through an enlarged volume defined by a re-breathing loop external to the housing via the first and second diversion passages. To selectively effect such diversion, an elliptical valve element is oriented within the housing at a 45° angle to both the first primary passage portion and the first diversion passage and disposed on the end of an actuation shaft aligned with the first diversion passage. The actuation shaft is adapted to selectively move between a normal operating mode position wherein the valve element occludes the mouth of the first diversion passage and a re-breathing mode position occluding communication between the first primary passage portion and second primary passage portion and diverting air flow through the first diversion passage into the re-breathing loop and back into the airway valve through the second diversion passage, which opens onto the second primary passage portion.

37 Claims, 4 Drawing Sheets

U.S. PATENT DOCUMENTS

| | | |
|---|---|---|
| 4,214,601 | 7/1980 | Sama . |
| 4,239,038 | 12/1980 | Holmes . |
| 4,241,756 | 12/1980 | Bennett et al. . |
| 4,267,832 | 5/1981 | Hakkinen . |
| 4,284,104 | 8/1981 | Beghini . |
| 4,333,450 | 6/1982 | Lester . |
| 4,454,893 | 6/1984 | Orchard . |
| 4,456,016 | 6/1984 | Nowacki et al. . |
| 4,462,397 | 7/1984 | Suzuki . |
| 4,463,755 | 8/1984 | Suzuki . |
| 4,493,339 | 1/1985 | Porter, Jr. . |
| 4,522,639 | 6/1985 | Ansite et al. . |
| 4,538,620 | 9/1985 | Nowacki et al. . |
| 4,543,935 | 10/1985 | Tuckey . |
| 4,606,339 | 8/1986 | Walther . |
| 4,622,964 | 11/1986 | Flynn . |
| 4,655,213 | 4/1987 | Rapoport et al. . |
| 4,699,137 | 10/1987 | Schroeder . |
| 4,712,580 | 12/1987 | Gilman et al. . |
| 4,941,476 | 7/1990 | Fisher . |
| 4,947,860 | 8/1990 | Fisher . |
| 4,986,310 | 1/1991 | Bailey et al. . |
| 5,002,050 | 3/1991 | McGinnis . |
| 5,005,568 | 4/1991 | Loescher et al. . |
| 5,020,532 | 6/1991 | Mahoney et al. . |
| 5,042,473 | 8/1991 | Lewis . |
| 5,072,729 | 12/1991 | DeVries . |
| 5,103,854 | 4/1992 | Bailey et al. . |
| 5,109,840 | 5/1992 | Daleiden . |
| 5,226,449 | 7/1993 | Zimmerly . |
| 5,233,998 | 8/1993 | Chowienczyk et al. . |
| 5,255,687 | 10/1993 | McKenna . |
| 5,299,579 | 4/1994 | Gedeon et al. . |
| 5,305,762 | 4/1994 | Acorn et al. ............................ 600/529 |
| 5,357,951 | 10/1994 | Ratner . |
| 5,438,981 | 8/1995 | Starr et al. . |
| 5,501,214 | 3/1996 | Sabo . |
| 5,630,411 | 5/1997 | Holscher . |
| 5,642,726 | 7/1997 | Owens et al. . |
| 5,647,355 | 7/1997 | Starr et al. . |

OTHER PUBLICATIONS

M. Gama de Abreu et al., "Reliability of the Partial $CO_2$ Rebreathing Technique for Measurement of Cardiac Output", Proceedings RC IEEE–EMBS & $14^{th}$ BMESI, 1995, pp. 4.15–4.16.

Marcelo Gama de Abreu et al., "Partial Carbon Dioxide Rebreathing: A Reliable Technique for Noninvasive Measurement of Nonshunted Pulmonary Capillary Blood Flow", Crit Care Med, vol. 25, No. 4, 1997, pp. 675–683.

B. Osterlund et al., "A New Method of Using Gas Exchange Measurements for the Noninvasive Determination of Cardiac Output: Clinical Experiences in Adults Following Cardiac Surgery", Acta Anaesthesiologica Scandinavica 39, 1995, pp. 727–732.

Andras Gedeon et al., "Noninvasive Cardiac Output Determined with a New Method Based on Gas Exchange Measurements and Carbon Dioxide Rebreathing: A Study in Animals/Pigs", Journal of Clinical Monitoring, vol. 8, No. 4, Oct. 1992, pp. 267–278.

A. Gedeon et al., "A New Method for Noninvasive Bedside Determination of Pulmonary Blood Flow", Medical & Biological Engineering & Computing, Jul. 1980, pp. 411–418.

Marcelo Gama de Abreu et al., "Measurement of Pulmonary Capillary Blood Flow for Trending Mixed Venous Blood Oxygen Saturation and Oxygen Delivery", 1 page.

Marcelo Gama de Abreu et al., "Is the Partial $CO_2$ Rebreathing Technique a Useful Tool for Trending Pulmonary Capillary Blood Flow During Adjustments of Peep?", 1 page.

Tilo Winkler et al., "Pulmonary Capillary Blood Flow by Parital $CO_2$ Rebreathing: A Simulation Study Using a Bicompartmental Model of Gas Exchange", 1 page.

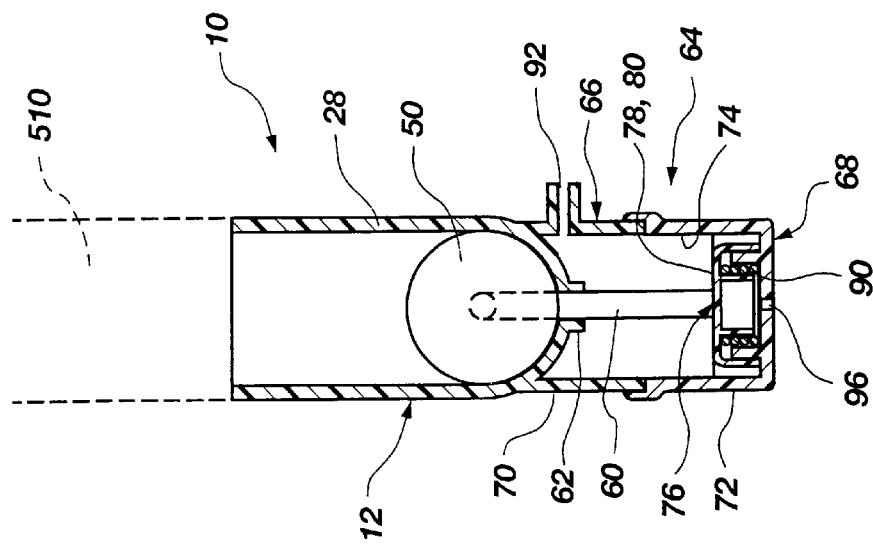
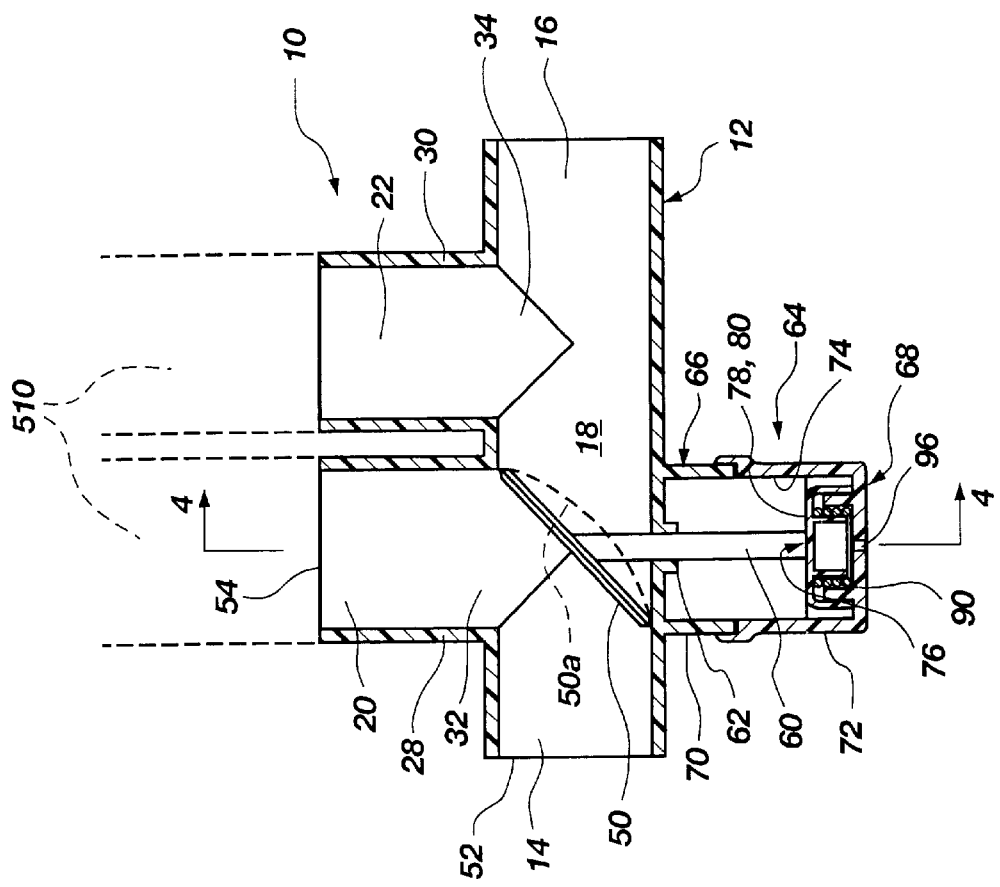

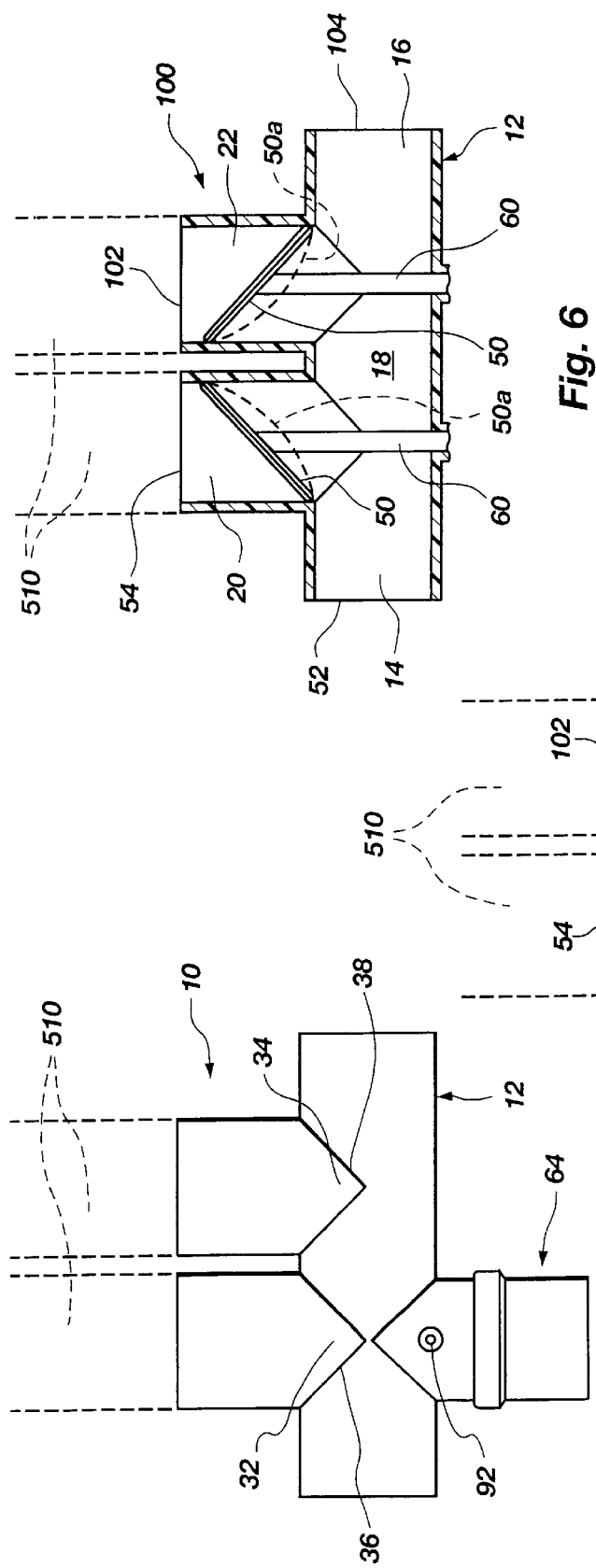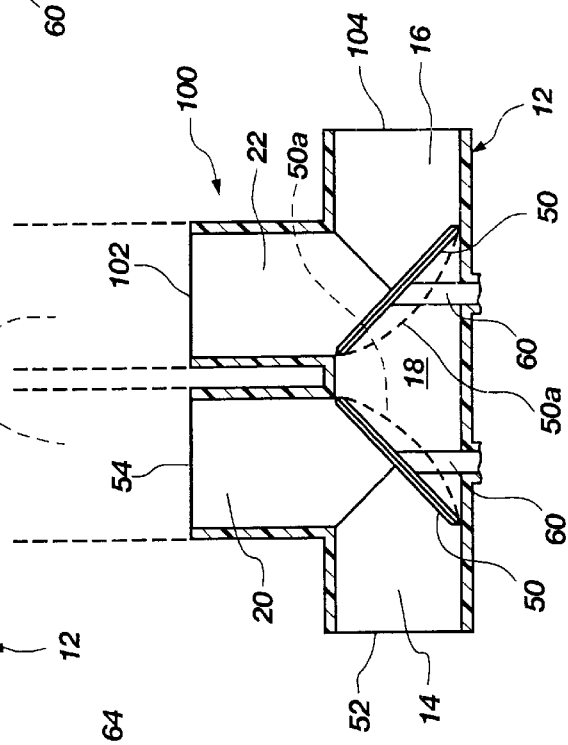

AIRWAY VALVE TO FACILITATE RE-BREATHING, METHOD OF OPERATION, AND VENTILATOR CIRCUIT SO EQUIPPED

BACKGROUND OF THE INVENTION

1. Field of the Invention

This invention relates to non-invasive approaches for determining cardiac output in patients, specifically to partial re-breathing techniques for determining cardiac output in patients, and most particularly to airway valves for initiating and terminating extension of the respiratory path volume, as well as ventilator circuits so equipped.

2. Statement of the Art

It is desirable, or even essential, to determine or monitor the cardiac output of a patient in many medical and surgical procedures. Invasive techniques well known and used in the art employ the use of catheters inserted at certain arterial points (e.g., femoral artery, jugular vein, etc.) to monitor blood temperature and pressure in order to determine cardiac output of the patient. Although capable of producing reasonably accurate results, the invasive nature of such procedures, with the attendant trauma and risk of infection, has demonstrated an unreasonably high potential for morbidity and mortality consequences.

Adolph Fick's measurement of cardiac output, first proposed in 1870, has served as the standard by which all other means of determining cardiac output have been evaluated since that date. Fick's well-known equation, written for $CO_2$, is:

$$Q = \frac{V_{CO_2}}{\left(C_{v_{CO_2}} - C_{a_{CO_2}}\right)}$$

where Q is cardiac output, $V_{CO2}$ is the amount of $CO_2$ excreted by the lungs and $C_{aCO2}$ and $C_{vCO2}$ are the arterial and venous $CO_2$ concentrations, respectively. Notably, the Fick Equation presumes an invasive method (i.e., catheterization) of calculating cardiac output because the arterial and mixed venous blood must be sampled in order to determine arterial and venous $CO_2$ concentrations.

It has previously been shown, however, that non-invasive techniques may be used for determining cardiac output while still using principles embodied in the Fick Equation. That is, expired $CO_2$ ("p$CO_2$") levels can be monitored to estimate arterial $CO_2$ concentrations and a varied form of the Fick Equation can be applied to evaluate observed changes in p$CO_2$ to estimate cardiac output. One use of the Fick Equation to determine cardiac output in non-invasive procedures requires the comparison of a "standard" ventilation event to a sudden change in ventilation which causes a change in expired $CO_2$ values and a change in excreted volume of $CO_2$. One commonly practiced means of providing a sudden change in effective ventilation is to cause the ventilated patient to re-breath a specified amount of previously exhaled air. This technique has commonly been called "re-breathing."

Prior methods of re-breathing have used the partial pressure of end-tidal $CO_2$ to approximate arterial $CO_2$ while the lungs act as a tonometer to measure venous $CO_2$. Such an approach to re-breathing has not proven to be satisfactory for determining cardiac output because the patient is required to breath directly into and from a closed volume in order to produce the necessary effect. However, it is usually impossible for sedated or unconscious patients to actively participate in inhaling and exhaling into a bag. The work of some researchers has demonstrated that the Fick Equation could be further modified to eliminate the need to directly calculate venous $P_{CO_2}$ ($P_{vCO_2}$) by assuming that the $P_{vCO_2}$ does not change within the time period of the perturbation—an assumption that could be made by employing the partial re-breathing method. (See, Capek et al., "Noninvasive Measurement of Cardiac Output Using Partial $CO_2$ Rebreathing", *IEEE Transactions On Biomedical Engineering*, Vol. 35, No. 9, Sep. 1988, pp. 653–661.)

Known partial re-breathing methods are advantageous over invasive measuring techniques because they 1) are non-invasive, 2) use the accepted Fick principle of calculation, 3) are easily automated, 4) require no patient cooperation and 5) allow cardiac output to be calculated from commonly monitored clinical signals. Thus, non-invasive cardiac output (NICO) techniques are rapidly gaining favor.

However, portions of known apparatus (i.e., ventilator circuits) used for partial re-breathing techniques employed in NICO, such as airway valves for initiating and terminating an extension of a patient's respiratory path through a conduit (tubing) loop or other reservoir, are of somewhat complex, relatively expensive construction, which render these somewhat contamination-prone and difficult to sterilize devices too expensive to be used as disposable units. In addition, conventional airway valves may unacceptably increase respiratory path volume when in normal operating (non-re-breathing) mode, may exhibit unduly high resistance to air flow in the normal operating mode, may require undesirably high energy levels to actuate, may not return in a fail-safe manner to the normal operating mode if actuation energy is removed, and their physical configurations may render them susceptible to malfunction responsive to the presence of moisture and other contaminants typically found in an airway circuit in close proximity to the patient. Finally, conventional airway valve designs may provide, or dictate, a fixed re-breathing volume, which fixed volume may not be optimum, or even suitable, for patients of various sizes and respiratory capacities.

Thus, it would be advantageous to provide a relatively simple and inexpensive, reliable, easy to fabricate, one-use (disposable) airway valve of a design which prevents cross-contamination between patients, minimizes any significant increase in respiratory path volume or air flow resistance therethrough when in a normal operating mode so as to not interfere with the function of the associated ventilator circuit, is usable with state-of-the art ventilator circuits without modification thereto and in a manner which is easy to actuate and control with minimal modifications to existing monitors, operates in a fail-safe manner so as to default to the normal operating mode, is resistant to contaminant-induced malfunctions, and easily accommodates variation in re-breathing volumes. Furthermore, it would be desirable for such an airway valve to introduce only minimal additional equipment bulk and weight in the vicinity of the patient.

BRIEF SUMMARY OF THE INVENTION

The airway valve of the present invention provides the above-enumerated desired advantages in form and function in contrast to conventional valve designs. The airway valve includes an outer housing defining a primary passage including first and second primary passage portions mutually directly communicating within the housing, and first and second diversion passages integral with the housing, each diversion passage opening onto a primary passage portion. The first diversion passage is oriented perpendicular to the first primary passage portion. The airway valve selectively controls diversion of normal operating mode air flow between the first primary passage portion and the second primary passage portion to initiate a re-breathing mode wherein air flow from the first primary passage portion passes into and through an enlarged volume defined by a re-breathing loop external to the housing via the first diversion passage and then back into to the second primary passage portion through the second diversion passage. To selectively effect such diversion, a valve element is oriented within the housing at a 45° angle to both the first primary passage portion and the first diversion passage and disposed on the end of an actuation shaft aligned with the first diversion passage. The actuation shaft is adapted to selectively move between a normal operating mode position wherein the valve element occludes the mouth of the first diversion passage and a re-breathing mode position wherein the valve element occludes communication between the first primary passage portion and second primary passage portion and diverts air flow through the first diversion passage for passage into the re-breathing loop and back into the airway valve through the second diversion passage, which opens onto the second primary passage portion. The actuation shaft is keyed against rotation and powered by a drive assembly preferably spring-biased toward the normal operating airway valve mode, the spring force being selectively overcome by application of positive air pressure through a pressure port to a closed cylinder volume to act on a piston element associated with the spring and on the opposite side of the spring therefrom. In one embodiment, all of the passages are cylindrical and of like size, and the valve element comprises an elliptical valve element. The first and second primary passage portions may be coaxial, and the first and second diversion passages both perpendicular thereto on the same or opposing sides of the first and second passages portions, or disposed at some other included rotational angle thereabout.

The airway valve may also have the second diversion passage oriented perpendicular to the second primary passage portion and optionally include another valve element oriented at a 45° angle to both the second primary passage portion and the second diversion passage and disposed on the end of an actuation shaft aligned with the second diversion passage. This actuation shaft is adapted to selectively move between a normal operating mode position wherein the second valve element occludes the mouth of the second diversion passage and a re-breathing mode position wherein the second valve element occludes communication between the second primary passage portion and the first primary passage portion and diverts air flow through the second diversion passage into the re-breathing loop and back into the airway valve through the first diversion passage, which opens onto the first primary passage portion. Due to respective opposing orientations of the valve elements, the diverted air flow for re-breathing is gradually turned in direction rather than undergoing an abrupt change. Furthermore, the valve elements may each be "dished" with a concavity so as to further guide the flow of gases to and from the diversion passages. The valve elements may be separately, or commonly, driven. The By placing a pressure port on the cylinder on the same side of the piston as the spring, a negative pressure (i.e., vacuum) may be employed to selectively actuate the shaft or shafts to drive the valve element or elements to the re-breathing mode.

A method of operating the airway valve of the invention and a ventilator circuit including the inventive valve are encompassed by the scope of the invention.

BRIEF DESCRIPTION OF THE SEVERAL VIEWS OF THE DRAWINGS

FIG. 3 is a top partial cross-sectional elevation of the airway valve of FIG. 1, shown in a re-breathing mode;

FIG. 4 is a side partial cross-sectional elevation of the airway valve of FIG. 1 taken across line 4—4 on FIG. 3, also shown in a re-breathing mode;

FIG. 5 is a top elevation of the airway valve of FIG. 1;

FIG. 6 is a top partial sectional elevation of a portion of a second embodiment of the airway valve of the invention in a normal operating mode;

FIG. 7 is a top partial sectional elevation of the airway valve embodiment of FIG. 6, but in a re-breathing mode.

DETAILED DESCRIPTION OF THE INVENTION

Figure 2:
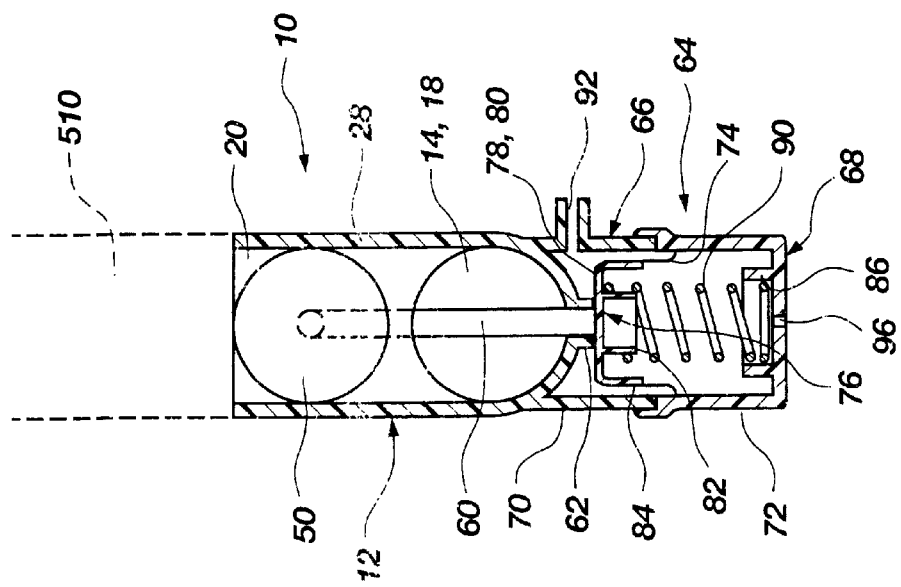
FIG. 2 is a side partial cross-sectional elevation of the airway valve of FIG. 1, taken across line 2—2, also shown in a normal operating mode.
Figure 1:
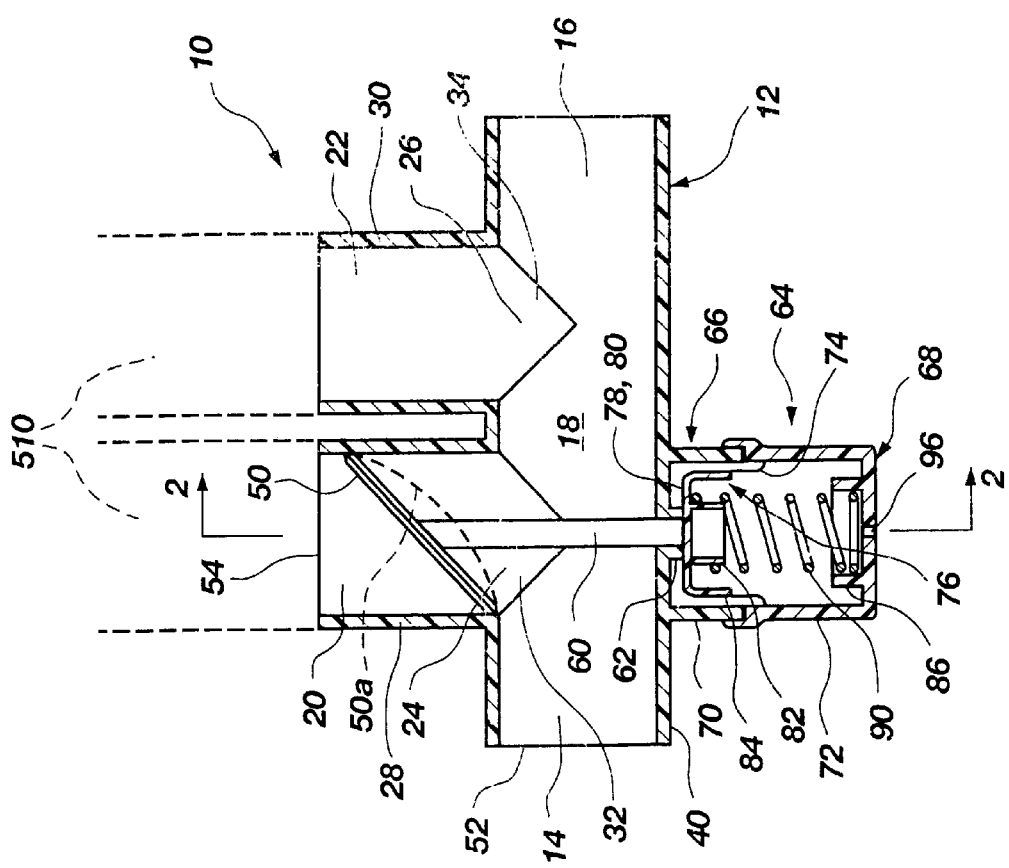
FIG. 1 is a top partial cross-sectional elevation of a first embodiment of the airway valve of the invention, shown in a normal operating mode.

Referring now to FIGS. 1 through 5 of the drawings, a first embodiment 10 of the airway valve of the present invention, and its operation, will be described.

Airway valve 10 includes a molded plastic housing 12 defining first and second coaxial primary passage portions 14 and 16 together comprising a primary passage 18, and first and second diversion passages 20 and 22 respectively opening onto first and second primary passage portions at 24 and 26, and oriented perpendicular to primary passage 18. Primary passage 18 and first and second diversion passages 20 and 22 are each cylindrical and of like internal diameter. It should be noted (see especially FIG. 5) that the walls 28 and 30 of diversion passages 20 and 22 include extensions 32 and 34 corresponding to cutouts 36 and 38 in the wall 40 of primary passage 18. The opposite side of housing 12 is similarly structured. Cooperating extensions 32, 34 and cutouts 36, 38 provide intersections of the first and second primary passage portions 14 and 16 with their associated first and second diversion passages 18 and 20 defining substantially constant diameters in both primary air flow and the perpendicular diversionary air flow directions.

An elliptical valve element 50, sized so as to occlude either first diversion passage 18 by blocking the bore thereof or communication between first primary passage portion 14 and second primary passage portion 16 by blocking the bore of first primary passage portion 14, is disposed at a 45° angle to both and facing the open bore mouths 52 and 54 of both. Elliptical valve element 50 is secured to an actuation shaft 60 which extends through an aperture 62 in the wall 40 of primary passage 18 and into a cylinder 64 defined by a sidewall 66, an end wall 68 and wall 40 of primary passage. Clearance between shaft 60 and aperture 62 is minimal, and a sealing element may preferably be provided therebetween if desired. Further, shaft 60 is asymmetrical or otherwise keyed against rotation so as to maintain valve element in the depicted orientation within housing 12. A first tubular portion 70 of cylinder 64 including a portion of sidewall 66 is preferably integrally molded with housing 12, while a second, cup-shaped portion 72 thereof including the remainder of sidewall 66 and end wall 68 is secured to the first portion 70 with flexible, preferably elastomeric skirt or diaphragm portion 74 of piston element 76 sealingly clamped therebetween. Central, rigid portion 78 of piston element 76 includes a circular face 80 transverse to shaft 60 and secured thereto and having skirt portion 74 sealingly secured thereto. Inner and outer coaxial, annular walls 82 and 84 extend transversely to circular face 80 facing away from primary passage 18, outer wall 84 being of greater length. Second portion 72 of cylinder 64 includes an annular, inwardly-facing wall 86 coaxial with inner and outer piston element walls 82 and 84 and intermediate in diameter between the inner diameter of outer annular piston element wall 84 and the outer diameter of inner annular piston element wall 82. Coil spring 90 extends coaxially with annular walls 82, 84 and 86 and is of a diameter intermediate that of walls 82 and 86. Pressure port 92 extends through the wall of first tubular portion 70 of cylinder sidewall 66 and so is on an opposite side of piston element 76 from coil spring 90. Vent aperture 96 is disposed in end wall 68.

In operation, airway valve 10 includes a spring-biased normal operating mode (FIGS. 1 and 2) wherein elliptical valve element 50 occludes first diversion passage 20, and air flow proceeds unimpeded through first primary passage 18. When it is desired to initiate the re-breathing mode, positive air pressure of a magnitude sufficient to overcome the force of spring 90 is applied to pressure port 92 under control of, for example, a patient monitor, and piston element 76 moves outward in cylinder 64, drawing shaft 60 outwardly from housing 12 into cylinder 64 and moving valve element 50 to the position shown in FIGS. 3 and 4 in first primary passage portion 14 wherein primary passage 18 is occluded and air flow is diverted through first diversion passage 20 into re-breathing loop 510 (see FIG. 8). Vent aperture 96 prevents trapping of air pressure on the spring side of piston element 76. In the re-breathing mode, slanted valve element 50 directs air flow between first primary passage portion 14 and first diversion passage 20 without an abrupt change in direction. If desired, valve element 50 may be "dished" or provided with a concavity as shown in broken lines at 50a facing open bore mouths 52 and 54 so as to further smooth the transition in air flow direction.

If desired, and as shown in a second embodiment 100 of the invention in FIGS. 6 and 7, a second valve element 50 facing the open bore mouths 102 and 104 of second primary passage portion 16 and second diversion passage 22 (and thus mutually back-to-back with the first valve element 50) may be disposed on the end of a second shaft 60 to alternately occlude second diversion passage 22 in the normal operating mode of valve 100 and second primary passage portion 16 in the re-breathing mode. The presence of two valve elements 50 will further smooth air flow within housing 12 in the re-breathing mode of the valve. The second valve element 50 may also be dished as shown in broken lines at 50a, to further smooth air flow. Both shafts 60 may be independently actuated with separate, spring-loaded piston element and cylinder assemblies driven by a supply of pressurized air through a two-branch manifold from a main conduit. Alternatively, both shafts may be driven in unison by a common piston element through a linkage. In FIGS. 6 and 7, features previously identified in FIGS. 1 through 5 by reference numerals are identified by the same reference numerals in FIGS. 6 and 7.

It is contemplated that airway valve 10 or 100 will be associated in use with a combined air flow and carbon dioxide sensor such as the Series 3 Pediatric/Adult Combined $CO_2$ Flow Sensor (Catalog No. 6719) offered by Novametrix Medical Systems, Inc. of Wallingford, Conn. ("Novametrix"). The structure and operation of the combined sensor is disclosed in U.S. Pat. No. 5,789,660, hereby incorporated herein by this reference. In the combined sensor, tubing is employed to tap pressures within differential pressure flow sensor portion as known in the art, while a saddle-configured, carbon dioxide sensor such as the CAPNOSTAT™ $CO_2$ sensor offered by Novametrix, is disposed over the carbon dioxide sensor portion so as to detect carbon dioxide through windows on each side thereof, also as known in the art. The structure and operation of the CAPNOSTAT™ sensor is disclosed in U.S. Pat. No. 5,793,044, hereby incorporated by this reference. Separate air flow sensors and carbon dioxide sensors may be employed in lieu of a combined sensor. Sensors functioning on other principles as well as sensors offered by other manufacturers may also be employed. It will be appreciated that the airway valve of the present invention has utility in any conventional or contemplated ventilator circuit employing a diversion loop, but that a ventilator incorporating the inventive valve as well as other components is contemplated as encompassed by the scope of the invention.

Figure 8:
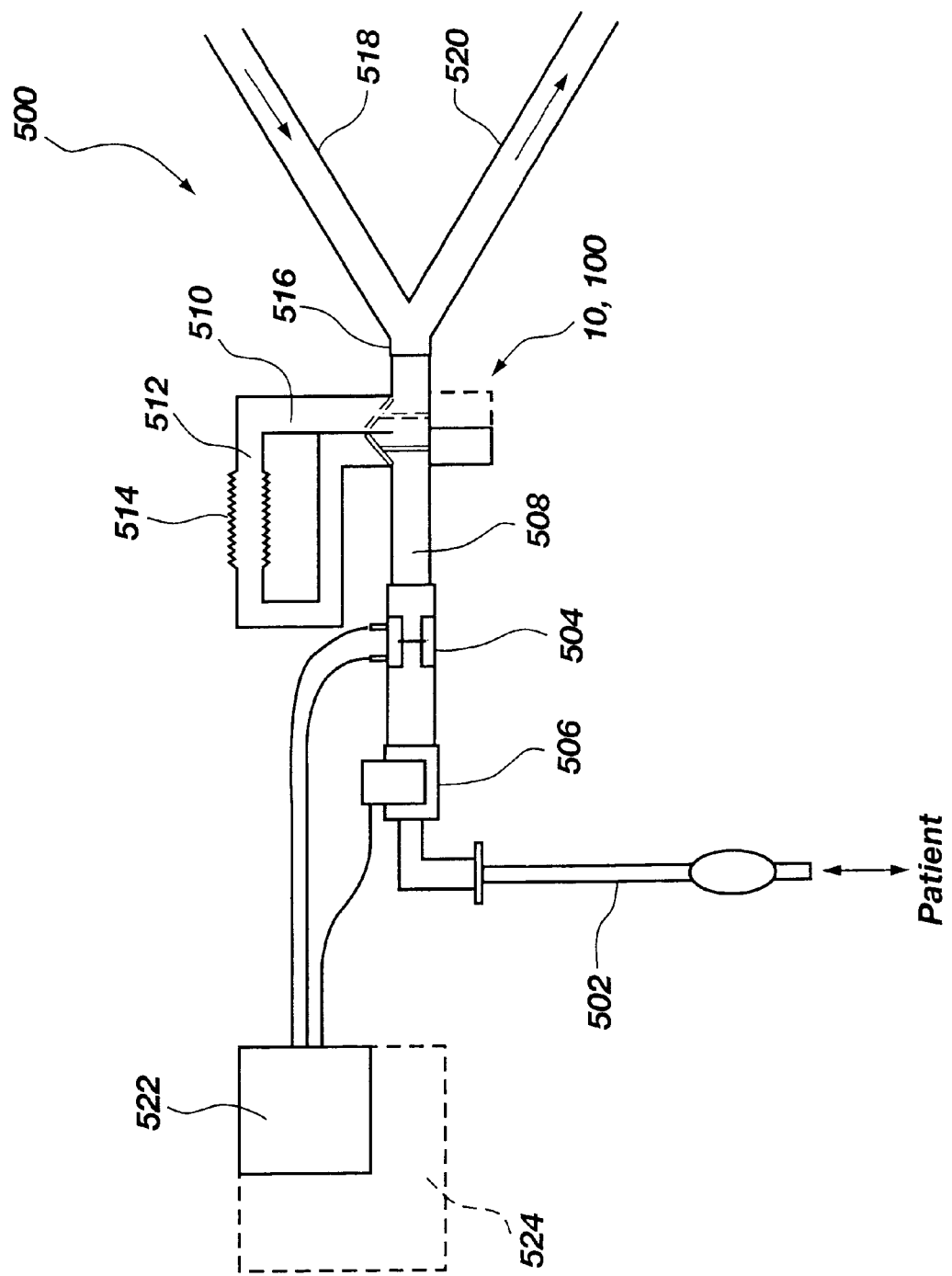
FIG. 8 is a schematic view of a ventilator circuit including the airway valve of the invention with associated flow and carbon dioxide sensors and processing equipment, as used with a patient.

Referring now to FIG. 8 of the drawings, a re-breathing equipped ventilator circuit or system 500, which causes a patient to inhale a gas mixture that includes carbon dioxide, is schematically illustrated. Exemplary ventilator circuit 500 includes a tubular airway 502 that communicates air flow to and from the lungs of a patient along a primary respiratory path. Tubular airway 502 may be placed in communication with the trachea of the patient by known intubation processes, or by connection to a breathing mask positioned over the nose and/or mouth of the patient. A flow meter 504, which is typically referred to as a pneumotachometer, and a carbon dioxide sensor 506, which is typically referred to as a capnometer, are disposed between tubular airway 502 and a length of hose 508, and are exposed to any air that flows through ventilator circuit 500. If desired, a combined air flow and carbon dioxide sensor as referenced above may be employed in lieu of discrete flow and gas sensors. Both ends of another length or loop of tubing 510, which may be referenced as defining a deadspace, a re-breathing volume or an alternative respiratory path 512, selectively communicate with hose 508. The two ends of tubing loop 510, and thus deadspace 512, are in communication with a two-mode airway valve 10 or 100 according to the present invention, which airway valve may be operated to selectively direct the flow of air through deadspace 512. Deadspace 512 may optionally include an expandable section 514, which may be provided by the use of corrugated tubing for tubing loop 510. A Y-piece 516, disposed on hose 508 opposite flow meter 504 and carbon dioxide sensor 506, facilitates the connection of an inspiratory hose 518 and an expiratory hose 520 to re-breathing circuit 500 and the flow communication of the inspiratory hose 518 and expiratory hose 520 with hose 508. During inhalation, gas flows into inspiratory hose 518 from the atmosphere or a ventilator (not shown). During normal breathing, airway valve 10 or 100 is maintained in the normal mode to prevent inhaled and exhaled air from flowing through deadspace 512. During re-breathing, airway valve 10 or 100 is positioned to direct the flow of exhaled and inhaled gases through deadspace 512. Processing unit 522, preferably incorporated in a patient monitor 524, is employed to process signals from sensors 504 and 506 and to control actuation of airway valve 10 or 100 by initiating and terminating application of positive air pressure to the airway valve 10 or 100 to sequence the system 500 between normal operating and re-breathing modes.

While the present invention has been described and illustrated in terms of certain specific embodiments, those of ordinary skill in the art will understand and appreciate that it is not so limited. Additions to, deletions from and modifications to these specific embodiments may be effected without departing from the scope of the invention as defined by the claims. Furthermore, features and elements from one specific embodiment may be likewise applied to another embodiment without departing from the scope of the invention as defined herein.

What is claimed is:

1. An airway valve for diverting respiratory flow from a primary path to an alternative path, comprising:
    a housing defining a primary passage including a first primary passage portion and a second primary passage portion, a first diversion passage perpendicular to the first primary passage portion and opening thereinto, and a second diversion passage opening into the second primary passage portion;
    a valve element oriented at a 45° angle to both the first primary passage portion and the first diversion passage and movable between a first position occluding the first diversion passage and a second position occluding communication between the first primary passage portion and the second primary passage portion.

2. The airway valve of claim 1, wherein the first primary passage portion and the first diversion passage are linear, cylindrical and of the same diameter, and the valve element is elliptical.

3. The airway valve of claim 1, wherein the valve element is secured to a shaft aligned with the first diversion passage and extending through a wall of the first primary passage portion to a spring-biased, differential pressure-driven actuation mechanism.

4. The airway valve of claim 3, wherein the first primary passage portion and the first diversion passage are linear, cylindrical and of the same diameter, and the valve element is elliptical.

5. The airway valve of claim 4, wherein the actuation mechanism includes a piston element to which the shaft is secured inside a cylinder bore defined by a wall structure, a spring inside the cylinder bore and a vent aperture between the cylinder bore and the exterior of the wall structure located on one side of the piston element and a port extending through the cylinder bore wall structure and communicating with the cylinder bore on an opposing side of the piston element.

6. The airway valve of claim 5, wherein the piston element further includes a flexible skirt extending to, and secured in sealing engagement with, the cylinder bore wall structure.

7. The airway valve of claim 6, wherein the flexible skirt is clamped between a first cylinder bore wall structure portion and a second cylinder bore wall structure portion to effect the sealing engagement.

8. The airway valve of claim 7, wherein the piston element includes a first protrusion thereon, an end wall of the cylinder bore wall structure includes a second protrusion facing the first protrusion and the spring is constrained between the two protrusions.

9. The airway valve of claim 8, wherein the spring is a coil spring, the first and second protrusions are annular, one protrusion is of an inner diameter greater than a diameter of the coil spring and the other protrusion is of an outer diameter greater than the coil spring diameter.

10. The airway valve of claim 1, wherein the second diversion passage is perpendicular to the second primary passage portion and further including another valve element oriented at a 45° angle to both the second primary passage portion and the second diversion passage and movable between a first position occluding the second diversion passage and a second position occluding communication between the first primary passage portion and the second primary passage portion.

11. The airway valve of claim 10, wherein the first and second primary passage portions are coaxial and the first and second diversion passages are mutually parallel.

12. The airway valve of claim 11, wherein the first and second passage portions and the first and second diversion passages are linear, cylindrical and of the same diameter, and the valve elements are elliptical.

13. The airway valve of claim 11, wherein the valve element is secured to a shaft aligned with the first diversion passage and extending through a wall of the first primary passage portion to a spring-biased, differential pressure-driven actuation mechanism and the another valve element is secured to another shaft aligned with the second diversion passage and extending though a wall of the second primary passage portion to a spring-biased, differential pressure-driven actuation mechanism.

14. The airway valve of claim 13, wherein the shaft and the another shaft are connected to the same spring-biased, differential pressure-driven actuation mechanism.

15. The airway valve of claim 14, wherein the valve elements each present a concave surface to a primary passage portion and a diversion passage with which they are respectively associated.

16. The airway valve of claim 1, wherein the valve element presents a concave surface to the first primary passage portion and the first diversion passage.

17. A method of operating an airway valve for diverting respiratory air flow from a primary path to an alternate path, comprising:
    providing a housing defining a primary passage including a first primary passage portion and a second primary passage portion, a first diversion passage and a second diversion passage, and a valve element associated with the first primary passage portion and the first diversion passage;
    opening communication between the first and second primary passage portions and closing communication between the first primary passage portion and the first diversion passage by placing a valve element in a first position within the first diversion passage; and closing communication between the first and second primary passage portions and
    opening communication between the first passage portion and the first diversion passage by placing the valve element in a second position within the primary passage.

18. The method of claim 17, further including providing another valve element
    associated with the second primary passage portion and the second diversion passage, and opening communication between the first and second primary passage portions and closing communication between the second primary passage portion and the second diversion passage by placing the another valve element in a first position within the second diversion passage; and
    closing communication between the first and second primary passage portions and opening communication between the second passage portion and the second diversion passage by placing the another valve element in a second position within the primary passage.

19. The method of claim 18, further comprising moving the first and second valve elements between their respective first and second positions simultaneously.

20. The method of claim 17, further including moving the valve element to the first position responsive to a spring bias, and moving the valve element to the second position responsive to a differential pressure sufficient to overcome the spring bias.

21. A ventilator circuit, comprising:
   a primary conduit arrangement for communicating respiratory flow to and from a patient along a primary respiratory path;
   a sensor device for measuring air flow incorporated in the primary conduit arrangement;
   a sensor device for measuring carbon dioxide incorporated in the primary conduit arrangement;
   a secondary conduit defining an alternative respiratory path;
   an airway valve for diverting respiratory flow from a portion of the primary respiratory path to the alternative respiratory path, comprising:
      a housing defining a primary passage in communication with the primary conduit arrangement and including a first primary passage portion and a second primary passage portion, a first diversion passage perpendicular to the first primary passage portion, opening thereinto and in communication with a first end of the secondary conduit, and a second diversion passage opening into the second primary passage portion and in communication with a second end of the secondary conduit;
      a valve element oriented at a 45° angle to both the first primary passage portion and the first diversion passage and movable between a first position occluding the first diversion passage and a second position occluding communication between the first primary passage portion and the second primary passage portion;
   structure for processing signals from the sensor devices; and
   structure for controlling actuation of the airway valve.

22. The ventilator circuit of claim 21, wherein the first primary passage portion and the first diversion passage are linear, cylindrical and of the same diameter, and the valve element is elliptical.

23. The ventilator circuit of claim 21, wherein the valve element is secured to a shaft aligned with the first diversion passage and extending through a wall of the first primary passage portion to a spring-biased, differential pressure-driven actuation mechanism.

24. The ventilator circuit of claim 23, wherein the first primary passage portion and the first diversion passage are linear, cylindrical and of the same diameter, and the valve element is elliptical.

25. The ventilator circuit of claim 24, wherein the actuation mechanism includes a piston element to which the shaft is secured inside a cylinder bore defined by a wall structure, a spring inside the cylinder bore and a vent aperture between the cylinder bore and the exterior of the wall structure located on one side of the piston element and a port extending through the cylinder bore wall structure and communicating with the cylinder bore on an opposing side of the piston element.

26. The ventilator circuit of claim 25, wherein the piston element further includes a flexible skirt extending to, and secured in sealing engagement with, the cylinder bore wall structure.

27. The ventilator circuit of claim 26, wherein the flexible skirt is clamped between a first cylinder bore wall structure portion and a second cylinder bore wall structure portion to effect the sealing engagement.

28. The ventilator circuit of claim 27, wherein the piston element includes a first protrusion thereon, an end wall of the cylinder bore wall structure includes a second protrusion facing the first protrusion and the spring is constrained between the two protrusions.

29. The ventilator circuit of claim 28, wherein the spring is a coil spring, the first and second protrusions are annular, one protrusion is of an inner diameter greater than a diameter of the coil spring and the other protrusion is of an outer diameter greater than the coil spring diameter.

30. The ventilator circuit of claim 21, wherein the second diversion passage is perpendicular to the second primary passage portion and further including another valve element oriented at a 45° angle to both the second primary passage portion and the second diversion passage and movable between a first position occluding the second diversion passage and a second position occluding communication between the first primary passage portion and the second primary passage portion.

31. The ventilator circuit of claim 30, wherein the first and second primary passage portions are coaxial and the first and second diversion passages are mutually parallel.

32. The ventilator circuit of claim 31, wherein the first and second passage portions and the first and second diversion passages are linear, cylindrical and of the same diameter, and the valve elements are elliptical.

33. The ventilator circuit of claim 31, wherein the valve element is secured to a shaft aligned with the first diversion passage and extending through a wall of the first primary passage portion to a spring-biased, differential pressure-driven actuation mechanism and the another valve element is secured to another shaft aligned with the second diversion passage and extending though a wall of the second primary passage portion to a spring-biased, differential pressure-driven actuation mechanism.

34. The ventilator circuit of claim 33, wherein the shaft and the another shaft are connected to the same spring-biased, differential pressure-driven actuation mechanism.

35. The ventilator circuit of claim 34, wherein the valve elements each present a concave surface to a primary passage portion and a diversion passage with which they are respectively associated.

36. The ventilator circuit of claim 21, wherein the valve element presents a concave surface to the first primary passage portion and the first diversion passage.

37. The ventilator circuit of claim 21, wherein the structure for processing sensor signals and the structure for controlling the airway valve are incorporated in a patient monitor.

* * * * *